United States Patent [19]

Motono

[11] Patent Number: 4,985,455

[45] Date of Patent: Jan. 15, 1991

[54] EXTERNAL PREPARATIONS FREE OF DISCOLORATION

[75] Inventor: Masahiro Motono, Kurume, Japan

[73] Assignee: Sansho Seiyaku Co., Ltd., Fukuoka, Japan

[21] Appl. No.: 223,590

[22] Filed: Jul. 25, 1988

[51] Int. Cl.$^5$ .................. A61K 31/35; A61K 7/42; A61K 7/44
[52] U.S. Cl. .................. 514/460; 424/59; 424/60; 514/58; 514/557; 514/844; 514/845; 514/846; 514/847; 514/937
[58] Field of Search .................. 424/59, 60, 62; 514/460, 844, 845, 846, 847, 58, 557

[56] References Cited

U.S. PATENT DOCUMENTS

| | | | |
|---|---|---|---|
| 3,880,875 | 4/1975 | Strobel et al. | 424/59 X |
| 4,465,629 | 8/1984 | Maughan | 424/195.1 |
| 4,742,066 | 5/1988 | Deckner et al. | 514/917 X |
| 4,837,019 | 6/1989 | Georgalas et al. | 424/59 X |
| 4,847,074 | 7/1989 | Hatae et al. | 514/58 X |

*Primary Examiner*—John W. Rollins
*Attorney, Agent, or Firm*—Jordan and Hamburg

[57] ABSTRACT

External preparations comprising, as active ingredients, kojic acid or a derivative thereof which also contain an ultraviolet absorber, β-cyclodextrin and ethylenediaminetetraacetic acid and have a controlled pH in the range from 4.0 to 5.0 show little discoloration during storage. In addition, discoloration of the preparation applied to the skin due to ultraviolet rays and other causes is also minimized, thus eliminating the trouble of contaminating clothes and other surrounding objects.

9 Claims, No Drawings

EXTERNAL PREPARATIONS FREE OF DISCOLORATION

BACKGROUND OF THE INVENTION

1. Field of the Invention

This invention relates to external preparations containing, as active ingredients, kojic acid or derivatives thereof which are free of discoloration with the passage of time.

2. Prior Art

Kojic acid and derivatives thereof are known to show inhibitory action against melanin which tends to be formed in the human skin. Also known are various liniments containing these substances as active ingredients. These include whitening cosmetics comprising kojic acid as an active ingredient (Japanese Patent Kokai No. 53-3538 and Japanese Patent Publication No. 56-18569), whitening cosmetics comprising, as active ingredients, a mono- or di-ester of kojic acid with an aliphatic carboxylic acid (Japanese Patent Kokai No. 56-7710 and Japanese Patent Publication No. 60-9722), whitening cosmetics comprising a kojic acid ester with an aromatic carboxylic acid, such as cinnamic and benzonic acids as active ingredients (Japanese Patent Publication No. 60-10005), and ointments to inhibit melanogenesis comprising kojic acid as an active ingredient (Japanese Patent Publication No. 61-10447).

As stated above, kojic acid and derivatives thereof are substances capable of effectively inhibiting the formation of melanin in the human skin. It is known that these substances are effective in making the human skin fair with no harmful effects to the skin when cosmetics and external preparations containing them as main ingredients are applied to human skin.

However, kojic acid or derivatives thereof manufactured as external preparations tend to become discolored with the passage of time during the steps of storage and distribution, which results in lowered value as commodities.

SUMMARY OF THE INVENTION

Our studies revealed that, when an ultraviolet absorber, β-cyclodextrin and ethylenediaminetetraacetic acid are incorporated in external preparations containing kojic acid or derivatives thereof as active ingredients and the pH is adjusted in the range from 4.0 to 5.0, kojic acid or derivatives thereof contained show no tendency of discoloration with passage of time, even after application to the skin. This invention was accomplished on the basis of these findings.

Thus, this invention relates to external preparations comprising kojic acid or derivatives thereof free of discoloration with the passage of time, the preparations also containing an ultraviolet absorber, β-cyclodextrin and ethylenediaminetetraacetic acid and the pH of the preparations being adjusted in the range from 4.0 to 5.0.

DESCRIPTION OF THE PREFERRED EMBODIMENTS

Kojic acid and derivatives thereof (active ingredients in the external preparations of this invention) are known substances capable of inhibiting the formation of melanin. As the derivatives of kojic acid, may be mentioned mono-esters with fatty acids such as kojic acid monopalmitate, kojic acid monobutylate, kojic acid monocaprylate and kojic acid monostearate (disclosed in Japanese Patent Kokai No. 61-77272), diesters with fatty acids such as kojic acid dipalmitate, kojic acid dibutylate, kojic acid dioleate and kojic acid distearate (disclosed in Japanese Patent Kokai No. 59-7776), kojic acid monocinnamate and kojic acid monobenzoate (disclosed in Japanese Patent Kokai No. 59-33207).

The external preparations of this invention contain the above-mentioned active ingredients capable of inhibiting the formation of melanin (kojic acid or derivatives thereof) in an amount of about 0.1 to 3 weight %. The external preparations herein mean general pharmaceutical preparations for external use, such as ointments, emulsions, lotions, creams, skin lotions and packs, which can be manufactured according to the methods commonly used for each type.

Any type of ultraviolet absorber may be used in the external preparations of this invention as a component to prevent discoloration, but preferred examples include phenyl salicylate, ethyl p-aminobenzoate, benzotriazole, 2-hydroxy-4-methoxybenzophenone, 2,2'-dihydroxy-4,4'-dimethoxybenzophenone and 2-hydroxy-4-methoxybenzophenone-5-sulfonic acid. These may be used either alone or in combination.

Discoloration of the external preparations of this invention comprising kojic acid or derivatives thereof can be effectively prevented by adjusting the pH in the range from 4.0 to 5.0. This can be effected by the use of a pH regulator such as citric acid.

Ethylenediaminetetraacetic acid (also called EDTA) which is used as another component to prevent discoloration of the external preparations of this invention with the passage of time is a substance widely employed as a chelating agent.

In the present invention, use of this chelator in combination with β-cyclodextrin and an ultraviolet absorber mentioned above effectively prevents discoloration of the external preparations comprising kojic acid or a derivative thereof, and also retards the skin absorption of active ingredients (kojic acid or a derivative thereof), thereby prolonging the action of the preparations on the skin.

The suitable contents of these components in the external preparations of this invention are 0.01 to 1.0 weight %, more preferably 0.2 to 0.5 weight %, for the ultraviolet absorber; 0.4 to 12 weight %, more preferably 1.0 to 5.0 weight %, for β-cyclodextrin; and 0.005 to 0.05 weight %, more preferably 0.01 to 0.03 weight %, for ethylenediaminetetraacetic acid.

These additives are added in proper amounts, together with kojic acid or derivatives thereof, to a commonly used base material, and any desired type of external preparations (e.g., ointments, emulsions, creams, lotions, skin lotions and packs) can be manufactured by known techniques. The preparations may also contain an anionic substance (e.g., sodium N-lauroyl-L-glutamate and sodium dipyrrolidonecarboxylate), a cationic substance (e.g., stearyltrimethylammonium chloride and cetyltrimethylammonium chloride), or an antioxidant (e.g., nicotinamide, nicotinic acid and natural vitamin E).

As apparent from the foregoing, the external preparations of this invention comprising kojic acid or derivatives thereof show little discoloration during storage. In addition, discoloration of the preparations applied to the skin due to ultraviolet rays and other causes is also minimized, thus eliminating the trouble of contaminating clothes and other surrounding objects.

EXAMPLE 1 (Skin lotion)

A mixture of 1.1.00 g of polyoxyethylene (60 E.O.) hardened castor oil, a perfume (a small amount), 15.00 g ethanol and 0.10 g ethyl p-oxybenzoate was mixed well by stirring until a clear solution was obtained. Separately, 0.10 g citric acid, 0.30 g sodium citrate, 0.50 g sodium N-lauroyl-L-glutamate, 4.00 g 1,3-butylene glycol, 0.01 g disodium ethylenediaminetetraacetate, 0.50 g kojic acid, 0.5 g 2-hydroxy-4-methoxybenzophenone-5-sulfionic acid and 1.00 g β-cyclodextrin were dissolved in pure water to make up 100 g of an aqueous solution. A skin lotion was prepared by adding the former solution to the latter with stirring.

EXAMPLE 2 (Emulsion)

A mixture of 0.50 g polyoxyethylene (20 E.O.) behenyl ether, 1.00 g polyoxyethylene (60 E.O.) sorbitol tetraoleate, 1.00 g lipophilic glycerol monostearate, 0.50 g stearic acid, 0.50 g behenyl alcohol, 10.00 g avocado oil, 0.02 g natural vitamin E, 0.20 g ethyl p-oxybenzoate, 1.00 g 2-hydroxy-4-methoxybenzophenone and 0.5 g 2,2'-dihydroxy-4,4'-dimethoxybenzophenone was heated to dissolve. Separately, a mixture of 5.00 g 1,3-butylene glycol, 0.10 g carboxyvinyl polymer, 0.02 g citric acid, 0.50 g sodium N-lauroyl-L-glutamate and 50 g pure water was heated until a clear solution was obtained. This aqueous solution was added with stirring to the oily liquid prepared above, and the resulting emulsion was cooled.

Disodium ethylenediaminetetraacetate (0.02 g), kojic acid 0.50 g, β-cyclodextrin (2.00 g), perfume (a small amount) and pure water were then added to make up a total weight of 100 g, and the mixture was stirred well to give an emulsion of pH 5.0.

EXAMPLE 3 (Skin cream)

A mixture of 100 g polyoxyethylene (60 E.O.) sorbitan monostearate, 1.50 g polyoxyethylene (60 E.O.) sorbitol tetraoleate, 1.50 g self-emulsifiable glycerol monosearate, 2.00 g bleached beeswax, 2.00 g paraffin, 3.00 g stearic acid, 3.00 g behenyl alcohol, 12.00 g almond oil, 0.04 g natural vitamin E, 0.10 g methylpolysiloxane, 0.20 g ethyl p-oxybenzoate, 2.00 g 2-hydroxy-4-methoxybenzophenone and 5.00 g liquid paraffin was heated until clear. Separately, a mixture of 5.00 g 1,3-butylene glycol, 0.50 g 2,2'-dihydroxy-4,4'-dimethoxybenzophenone, 0.03 g citric acid, 0.50 g sodium N-lauroyl-L-glutamate and pure water (a total weight of 100 g) was heated until clear solution was obtained. This aqueous solution was added with stirring to the oily liquid prepared above, and the resulting emulsion was cooled.

Disodium ethylenediaminetetraacetate (0.02 g), kojic acid (2.00 g), β-cyclodextrin (8.00 g) and perfume (a small amount) were then added, and the mixture was stirred well to give a skin cream of pH 5.0.

EXAMPLE 4 (Cream pack)

A mixture of 1.00 g polyoxyethylene (20 E.O.) behenyl ether, 2.00 g polyoxyethylene (40 E.O.) sorbitol tetraoleate, 2.00 g lipophilic glycerol monostearate, 3.00 g bleached beeswax, 2.00 g stearic acid, 3.00 g behenyl alcohol, 25.00 g squalane, 10.00 g glycerol octanoate, 0.04 g natural vitamin E, 0.20 g ethyl p-oxybenzoate, and 0.5 g 2,2'-dihydroxy-4,4'-dimethoxybenzophenone was heated until clear. Separately, a mixture of 5.00 g 1,3-butylene glycol, 1.50 g sodium di-pyrrolidonecarboxylate and 50 g pure water was heated until a clear solution was obtained. This aqueous solution was added with stirring to the oily liquid prepared above, and the resulting emulsion was cooled. Disodium ethylenediaminetetraacetate (0.02 g), citric acid (0.04 g), kojic acid (1.00 g), β-cyclodextrin (4.00 g), a perfume (a small amount) and pure water were then added to make up a total weight of 1.00 g, and the mixture was stirred well to give a cream pack of pH 4.70.

TEST EXAMPLE

1. Test samples (a) A lotion composed of 1.00 % polyoxyethylene (60 E.O.) hydrogenated castor oil, a perfume (a small amount), 15.00 % ethanol, 0.1 % ethyl p-oxybenzoate, 0.1 % citric acid, 0.3 % sodium citrate, 4.0 % 1,3-butylene glycol, 1.0 % kojic acid and 78.5 % pure water (control sample).

(b) Lotion (a) supplemented with 0.01 % ethylenediaminetetraacetic acid (a reference sample).

(c) Lotion (a) supplemented with 0.50 % 2-hydroxy-4-methoxybenzophenonesulfonic acid (a reference sample).

(d) Lotion (a) supplemented with 1.0 % β-cyclodextrin (a reference sample).

(e) Lotion (a) supplemented with 0.01 % ethylenediaminetetraacetic acid, 0.5 % 2-hydroxy-4-methoxybenzophenonesulfonic acid and 1.0 % β-cyclodextrin (sample of this invention). (Percentages shown above are all on a weight basis, and the pH of lotion (e) is 4.5.)

2. Method of test

Each of the above test samples (100 ml) was placed in a beaker and irradiated with ultraviolet rays (UV A and UV B) at a rate of 25 J/cm$^2$, and the degree of discoloration after ten days was measured using a color difference meter (Model Z-1001DP, Nippon Denshoku Kogyo Co., Ltd.).

3. Results of test

The result obtained is summarized in the table below.

| Test Samples | ΔE |
| --- | --- |
| (a) Control sample | 9.38 |
| (b) Reference sample | 6.05 |
| (c) Reference sample | 4.30 |
| (d) Reference sample | 4.55 |
| (e) Sample of this invention | 1.22 |

As shown in the table, discoloration was significantly prevented with sample (e) of this invention.

What is claimed is:

1. A topical composition free of discoloration with the passage of time comprising at least 0.1 weight percent of kojic acid or a derivative thereof; at least 0.01 weight percent of an ultraviolet absorber; at least 0.4 weight percent of β-cyclodextrin; and at least 0.005 weight percent of ethylenediaminetetraacetic acid, said composition having a pH in the range of from 4.0 to 5.0.

2. A topical composition as in claim 1, comprising 0.1 to 3 weight percent of said kojic acid or a derivative thereof; 0.01 to 1 weight percent of said ultraviolet absorber; 0.4 to 12 weight percent of said β-cyclodextrin; and 0.005 to 0.05 weight percent of said ethylenediaminetetraacetic acid.

3. A topical composition as in claim 1, comprising 0.1 to 3 weight percent of said kojic acid or derivative thereof; 0.2 to 0.5 weight percent of said ultraviolet absorber; 1.0 to 5.0 weight percent of said β-cyclodextrin; and 0.01 to 0.03 weight percent of said ethylenediaminetetraacetic acid.

4. A topical composition as in claim 1, further comprising a pH regulator to adjust the p of said composition in said range of from 4.0 to 5.0.

5. A topical composition as in claim 4, herein said pH regulator comprises citric acid.

6. A topical composition as in claim 1, wherein said ultraviolet absorber is at least one member selected from the group consisting of 2-hydroxy-4-methoxybenzophenone, 2-hydroxy-4-methoxybenzophenone-5-sulfonic acid, phenyl salicylate, benzotriazole, ethyl p-aminobenzoate and 2,2'-dihydroxy-4,4'-dimethoxybenzophenone.

7. A topical composition as in claim 1, in a form selected from the group consisting of an ointment, an emulsion, a lotion, a skin cream, a skin lotion and a cream pack.

8. A topical composition as in claim 1, further comprising at least one member selected from the group consisting of an anionic substance, a cationic substance and an antioxidant.

9. A topical composition as in claim 8, wherein said anionic substance is selected from the group consisting of sodium N-lauroyl-L-glutamate and sodium di-pyrrolidonecarboxylate, said cationic substance is selected from the group consisting of stearyltrimethylammonium chloride and cetyltrimethylammonium chloride, and said antioxidant is selected from the group consisting of nicotinamide, nicotinic acid and natural vitamin E.

* * * * *